(12) United States Patent
Osada et al.

(10) Patent No.: US 8,029,824 B2
(45) Date of Patent: Oct. 4, 2011

(54) HYDROGEL OF (SEMI) INTERPENETRATING NETWORK STRUCTURE AND PROCESS FOR PRODUCING THE SAME

(75) Inventors: Yoshihito Osada, Sapporo (JP); Jian Ping Gong, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 10/513,070

(22) PCT Filed: Apr. 10, 2003

(86) PCT No.: PCT/JP03/04556
§ 371 (c)(1),
(2), (4) Date: Feb. 11, 2005

(87) PCT Pub. No.: WO03/093337
PCT Pub. Date: Nov. 13, 2003

(65) Prior Publication Data
US 2005/0147685 A1   Jul. 7, 2005

(30) Foreign Application Priority Data
May 1, 2002 (JP) .............. PCT/JP02/04358

(51) Int. Cl.
*A61K 9/14* (2006.01)
(52) U.S. Cl. ..................................... 424/486
(58) Field of Classification Search ............ 424/486, 424/487, 1.85, 130.1, 600; 525/301; 521/25
See application file for complete search history.

(56) References Cited

U.S. PATENT DOCUMENTS

| | | | |
|---|---|---|---|
| 4,071,508 A | 1/1978 | Steckler | |
| 5,264,495 A | 11/1993 | Irie et al. | |
| 5,644,049 A | 7/1997 | Giusti et al. | |
| 6,235,433 B1 | 5/2001 | Amano et al. | |
| 6,271,278 B1 * | 8/2001 | Park et al. | 521/150 |
| 6,613,030 B1 | 9/2003 | Coles et al. | |
| 6,641,569 B1 | 11/2003 | Coles et al. | |
| 7,279,507 B2 | 10/2007 | Hu et al. | |
| 2001/0044482 A1 | 11/2001 | Hu et al. | |
| 2002/0022884 A1 | 2/2002 | Mansmann | |
| 2008/0119930 A1 | 5/2008 | Osada et al. | |

FOREIGN PATENT DOCUMENTS

| | | |
|---|---|---|
| JP | 03-079608 A | 4/1991 |
| JP | 03-165774 A | 7/1991 |
| JP | 06 200224 A | 7/1994 |
| JP | 8-319231 A | 12/1996 |
| JP | 10-500148 A | 1/1998 |
| JP | 10-032019 A | 2/1998 |
| JP | 2000-231127 A | 8/2000 |
| JP | 2002-351806 A | 12/2000 |
| JP | 2001-131249 A | 5/2001 |
| JP | 2002-501563 A | 1/2002 |
| JP | 2002-105344 A | 4/2002 |
| JP | 2002-212452 A | 7/2002 |
| WO | WO 92/13566 A1 | 8/1992 |
| WO | WO 94/01468 A | 1/1994 |
| WO | WO 00/07636 A | 2/2000 |

OTHER PUBLICATIONS

Zhang et al., Macromolecules 2000, 33, 102-107.*
Burugapalli et al., J. Appl Polym Sci, 2001, 82, pp. 217-227.*
Bigi et al., Biomaterials, 22, 2001, pp. 763-768.*
English translation of International Preliminary Examination Report Form PCT/IPEA/409 in International Application No. PCT/JP02/004556.
Database WPI Section Ch, Week 199433, Thomas Scientific, London, GB; AN 1994-269661 XP002490495 & JP 06 200224 A (Nitto Chem. Ind. Co. Ltd.) Jul. 19, 1994 abstract.
Nishimura et al., "Controlled Adsorption of Metal Ions by Thermo-Sensitive Hydrogels", *Polymer Preprints*, vol. 49, No. 12, p. 3471-3472, Sep. 8, 2000, Japan.
Corkhill et al., "Towards a synthetic articular cartilage", *J. Biomater. Sci. Polymer Edn.*, vol. 4, No. 6, (1993), pp. 615 to 630.
Santin et al., "Synthesis and characterization of a new interprenetrated poly(2-hydroxyethylmethacrylate)-gelatin composite polymer", *Biomaterials*, vol. 17, No. 15, (1996), pp. 1459 to 1467.
Kobayashi et al., "Preliminary study of polyvinyl alcohol-hydrogel (PVA-H) artificial meniscus", *Biomaterials*, vol. 24, pp. 639 to 647 (2003).
Grassman et al., "Morphogenetic Control of Calcite Crystal Growth in Sulfonic Acid Based Hydrogels", *Chem. Eur. J.*, vol. 9, No. 6, (2003), pp. 1310 to 1316.
Burugapalli et al., "Effect of composition of interpenetrating polymer network hydrogels based on poly(acrylic acid) and gelatin on tissue response: a quantitative in vivo study" *Biomedical Materials Research*, vol. 68A, No. 2, Feb. 1, 2004, pp. 210 to 218.

* cited by examiner

*Primary Examiner* — Michael G Hartley
*Assistant Examiner* — James Rogers
(74) *Attorney, Agent, or Firm* — Holtz, Holtz, Goodman & Chick, PC

(57) ABSTRACT

A hydrogel of the semi-interpenetrating network structure or interpenetrating network structure, characterized in that the hydrogel is one formed from a first monomer ingredient at least 10 mol % of which is accounted for by a charge-possessing unsaturated monomer, the molar ratio of the first monomer ingredient to the second monomer ingredient being from 1/2 to 1/100, and that the second monomer ingredient has been polymerized and crosslinked to a lower degree of crosslinking than the first monomer ingredient. The hydrogel is usable in a diaper, sanitary good, sustained-release agent, construction material, building material, communication material, soil conditioner, contact lens, ocular lens, hollow fiber, artificial cartilage, artificial organ, material for fuel cells, battery diaphragm, impact-resistant material, cushion, etc.

14 Claims, 7 Drawing Sheets

(a)          (b)

HYDROGEL OF (SEMI) INTERPENETRATING NETWORK STRUCTURE AND PROCESS FOR PRODUCING THE SAME

This application is a U.S. National Phase Application under 35 USC 371 of International Application PCT/JP03/04556 filed Apr. 10, 2003, which is incorporated herein in its entirety by this reference.

TECHNICAL FIELD

This invention relates to a hydrogel of a semi-interpenetrating structure or an interpenetrating structure, having a high content of water and an excellent mechanical strength, and a process for producing the same.

BACKGROUND ART

Polymer gels possess a number of interesting properties which solids or liquids cannot singly have, such as low surface friction property, permeability for materials and organism-like positive motorial property against external stimulations. When an attempt is made to utilize such gels for daily life or in the medical and industrial fields, exploiting such properties, however, most of them currently lack mechanical strength and are brittle, apart from some of them such as polyvinyl alcohol (PVA) and poly-2-hydroxyethyl methacrylate (PHEMA) gels. If a gel (hydrogel, in particular) possessing a high strength were produced and if the principles thereof were understood and the mechanical strength of thereof were freely controlled, highly functional biomaterials could be developed at a practical level not only for livelihood and industrial utilizations but as well for applications in artificial blood vessels exploiting the permeability for materials of the gels and artificial arthrodial cartilages of gels having low-friction surfaces, with an expectation that the values of use of the polymer gels would drastically be increased.

Accordingly, this invention aims to provide a hydrogel having a high content of water and an excellent mechanical strength while exploiting the characteristics of a gel for retaining shapes.

DISCLOSURE OF THE INVENTION

This invention (1) is a hydrogel of a semi-interpenetrating network structure or an interpenetrating network structure, obtainable by polymerizing and crosslinking a first monomer component to form a network structure; introducing a second monomer component into the network structure; and polymerizing and optionally crosslinking the second monomer component, characterized in that 10 mol % or more of the first monomer component is an unsaturated monomer having an electric charge, 60 mol % or more of the second monomer component is an electrically neutral unsaturated monomer, the molar ratio of the first monomer component to the second monomer component is from 1:2 to 1:100, and when the second monomer component is polymerized and crosslinked, the degree of crosslinking is set to be lower than the degree of crosslinking of the first monomer component being polymerized and crosslinked.

This invention (2) is the hydrogel according to the invention (1), wherein the unsaturated monomer having an electric charge is an unsaturated monomer having an acidic group and/or a basic group.

This invention (3) is the hydrogel according to the invention (2), wherein the acidic group is selected from the group consisting of a carboxyl group, a phosphate group and a sulfonic group.

This invention (4) is the hydrogel according to the invention (3), wherein the unsaturated monomer having an acidic group is 2-acrylamido-2-methylpropane sulfonic acid, acrylic acid, methacrylic acid or a salt thereof.

This invention (5) is the hydrogel according to any one of the inventions (1) to (4), wherein the electrically neutral unsaturated monomer is acrylamide, N-isopropyl acrylamide, vinylpyridine, styrene, methyl methacrylate, a fluorine-containing unsaturated monomer (for example, trifluoroethyl acrylate), hydroxyethyl acrylate or vinyl acetate.

This invention (6) is the hydrogel according to any one of the inventions (1) to (5), wherein the hydrogel further contains a metal ion, and at least part of the first monomer component and the second monomer component has a group capable of forming a complex with the metal ion.

This invention (7) is the hydrogel according to any one of the inventions (1) to (6), wherein the network structure based on the first monomer component has a degree of crosslinking of 0.1 to 50 mol % and the network structure based on the second monomer component has a degree of crosslinking of 0.001 to 20 mol %.

This invention (8) is the hydrogel according to any one of the inventions (1) to (7), which has a water content of 10% or more.

This invention (9) is the hydrogel according to any one of the inventions (1) to (8), which has a compression stress at rupture of 1 to 100 MPa.

This invention (10) is the hydrogel according to any one of the inventions (1) to (9), which has a tensile stress at rupture of 0.1 to 100 MPa.

This invention (11) is the hydrogel according to any one of the inventions (1) to (10), which is stress-dispersing.

This invention (12) is the hydrogel according to any one of the inventions (1) to (11), which has a degree of shrinkage of 20 to 95%.

This invention (13) is an article using the hydrogel of any one of the inventions (1) to (12).

This invention (14) is the article according to the invention (13), which is selected from a diaper, a sanitary product, a sustained-release material, a construction material, a building material, a communication material, a soil conditioner, a contact lens, an intraocular lens, a hollow fiber, an artificial cartilage, an artificial organ, a material for fuel cells, a battery diaphragm, an impact-resistant material and a cushion.

This invention (15) is a process for producing a hydrogel of a semi-interpenetrating network structure or an interpenetrating network structure, comprising the steps of:

polymerizing and crosslinking a first monomer component, of which 10 mol % or more is an unsaturated monomer having an electric charge, to form a first network structure; and introducing a second monomer component, of which 60 mol % or more is an electrically neutral unsaturated monomer, into the first network structure and then polymerizing the second monomer component thereby to form a polymer in the first network structure; or optionally, further crosslinking the second monomer component thereby to form a second network structure in the first network structure, wherein when the second monomer component is polymerized and crosslinked, the degree of crosslinking is set to be lower than the degree of crosslinking of the first monomer component being polymerized and crosslinked and wherein the molar ratio of the first monomer component to the second monomer component is from 1:2 to 1:100.

This invention (16) is the process according to the invention (15), wherein the unsaturated monomer having an electric charge is an unsaturated monomer having an acidic group and/or a basic group.

This invention (17) is the process according to the invention (16), wherein the acidic group is selected from the group consisting of a carboxyl group, a phosphate group and a sulfonic group.

This invention (18) is the process according to the invention (17), wherein the unsaturated monomer having an acidic group is 2-acrylamido-2-methylpropane sulfonic acid, acrylic acid, methacrylic acid or a salt thereof.

This invention (19) is the process according to any one of the inventions (15) to (18), wherein the electrically neutral unsaturated monomer is acrylamide, N-isopropyl acrylamide, vinylpyridine, styrene, methyl methacrylate, a fluorine-containing unsaturated monomer (for example, trifluoroethyl acrylate), hydroxyethyl acrylate or vinyl acetate.

This invention (20) is the process according to any one of the inventions (15) to (19), wherein the hydrogel further contains a metal ion, and at least part of the first monomer component and the second monomer component has a group capable of forming a complex with the metal ion.

This invention (21) is the process according to any one of the inventions (15) to (20), wherein the network structure based on the first monomer component has a degree of crosslinking of 0.1 to 50 mol % and the network structure based on the second monomer component has a degree of crosslinking of 0.001 to 20 mol %.

This invention (22) is the process according to any one of Claims (15) to (21), wherein the hydrogel has a water content of 10% or more.

This invention (23) is the process according to any one of the inventions (15) to (22), wherein the hydrogel has a compression stress at rupture of 1 to 100 MPa.

This invention (24) is the process according to any one of the inventions (15) to (23), wherein the hydrogel has a tensile stress at rupture of 0.1 to 100 MPa.

This invention (25) is the process according to any one of the inventions (15) to (24), wherein the hydrogel is stress-dispersing.

This invention (26) is the process according to any one of the inventions (15) to (25), wherein the hydrogel has a degree of shrinkage of 20 to 95%.

BEST MODE FOR CARRING OUT THE INVENTION

First of all, technical terms as used herein will be defined.

The term "hydrogel of an interpenetrating network structure" refers to a gel in which a network structure as a base is uniformly entwined with another network structure throughout the gel, with a result that multiple network structures are formed within the gel. For example, as shown in FIG. 1, such a hydrogel is composed of a first network structure A having multiple crosslinking points 1 and a second network structure B having multiple crosslinking points 2, these first and second network structures A and B being physically entwined with each other through their networks.

The term "hydrogel of a semi-interpenetrating network structure" refers to a gel in which a network structure as a base is uniformly entwined with a linear polymer throughout the gel, with a result that multiple network structures are formed within the gel. For example, as shown in FIG. 2, such a gel is composed of a first network structure C having multiple crosslinking points 3 and a linear polymer D, the first network structure C and the linear polymer D being physically entwined with each other through their networks.

Figure 1:
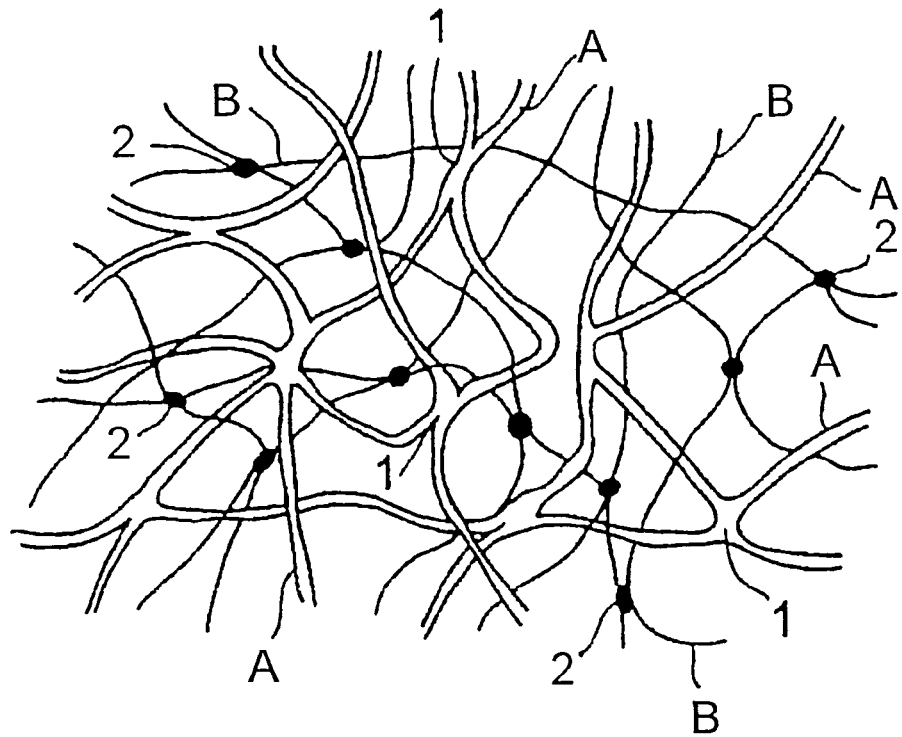
FIG. 1 shows a hydrogel of an interpenetrating network structure in which a network structure formed by polymerizing and crosslinking a first monomer component (first network structure) and another network structure formed by polymerizing and crosslinking a second monomer component (second network structure) are physically entwined with each other through their networks; in other words, a double network type gel (DN gel), wherein A denotes the first network structure, B denotes the second network structure and 1 and 2 denote crosslinking points.
Figure 2:
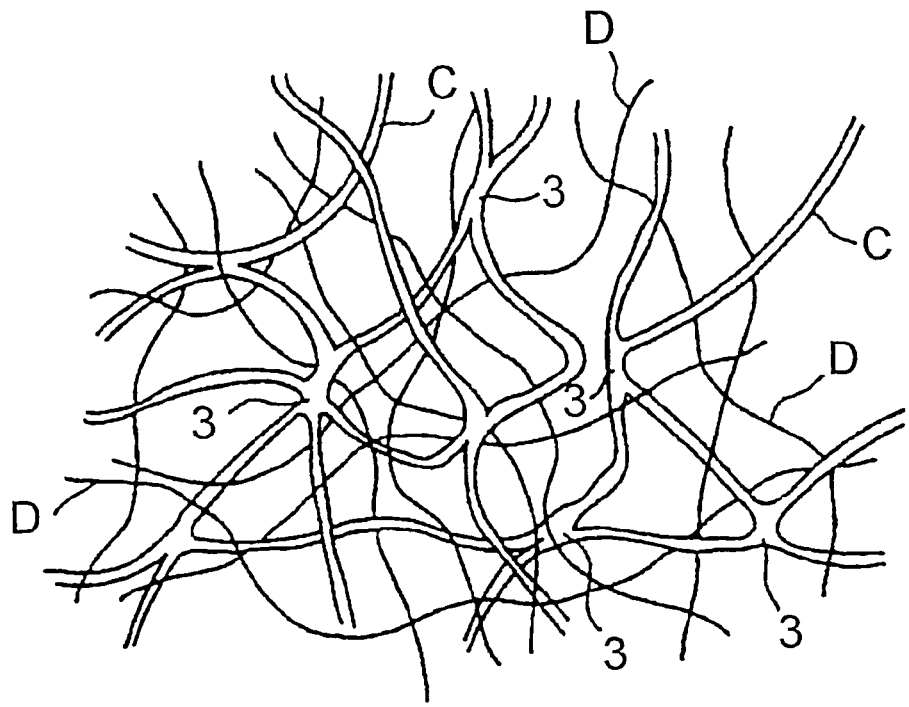
FIG. 2 shows a hydrogel of an semi-interpenetrating network structure (DN gel) in which a first network structure and a linear polymer formed by polymerizing a second monomer component are physically entwined with each other through their networks (DN gel), wherein C denotes the first network structure, D denotes the linear polymer and 3 denote crosslinking points.

In FIGS. 1 and 2, the first network structures A and C are drawn in bolder lines than the second network structure B and the linear polymer D, but only for convenience. In addition, "hydrogel of an interpenetrating network structure" and "hydrogel of a semi-interpenetrating network structure" conceptually encompass gels, not only of the double network type, but also of a triple, quadruple or more network type.

The term "degree of crosslinking" refers to a ratio of the mol concentration of a crosslinker to the mol concentration of a charged monomer, which is expressed in percentage. In reality, a slight amount of monomer may fail to be involved in polymerization or a slight amount of crosslinker may fail to be involved in crosslinking; in such cases, however, the degree of crosslinking herein is to be defined as above.

The term "water content" is to be given by:

water content=weight of water/(weight of water+ weight of dry gel)×100(%).

As used herein, "hydrogel" refers to a gel in which solvent is water; however, an inappreciable amount of water-soluble solvent (an alcohol, for example) etc. may be included.

"Compression stress at rupture" is calculated by the formula (force at rupture under compression/original cross sectional area) and "compression strain at rupture" is calculated by the formula (original length−length at rupture under compression)/original length×100%. These may be determined according to Method A below.

Method of Measurement A:

Gel is sliced into a disk 9 mm in diameter and 5 mm in thickness, and the gel is interposed between two flat plates and compressed using a TENSILON® tensile tester (manufactured by ORIENTEC, Model: RTC-1310A) for compression stress at rupture. The rate of compression is to be 10% per minute.

"Tensile stress at rupture" is calculated by the formula (force at rupture under tension/original cross sectional area) and "tensile strain at rupture" is calculated by the formula (length at rupture under tension−original length)/original length×100%. These may be determined according to Method B below.

Method of Measurement B:

Gel is sliced into a rectangle 5 cm in length, 5 mm in width and 3 mm in thickness, and the gel is grabbed at the both ends using a special-purpose fixture (chuck) and subjected to a test with a TENSILON® tensile tester (manufactured by ORIENTEC, Model: 1310A). The stress at rupture is designated a tensile stress at rupture σ. The rate of tension is to be 10% per minute.

The term "degree of swelling" refers to a value given by the formula:

degree of swelling=weight of swollen gel($W_W$)/weight of dry gel($W_D$)

The term "degree of shrinkage" refers to a ratio of the weight of gel equilibrated and swollen in saline water to the weight of gel equilibrated and swollen in pure water, which is expressed in percentage, to be determined according to Method C below.

Method of Measurement C:

Gel is cut to a size 2×2×2 cm³, placed in 500 ml of distilled water at 20° C., and equilibrated and swollen for one day. After being equilibrated and swollen, the gel is removed from the water and weighed with a balance. The gel is then placed in 500 ml of 0.1 mol/l aqueous solution of sodium chloride at 20° C., immersed for one day for equilibrium and swelling and then removed before weighing.

The term "water-insoluble monomer" refers a monomer, 0.1 g or less of which dissolves, when introduced in an amount of 1 g into 100 ml of water at normal temperature and pressure. The term "water-soluble monomer" refers to a monomer, dissolution of which exceeds the above value at normal temperature and pressure.

The hydrogel according to this invention will now be described. A first feature of this invention is that 10 mol % or more of the first monomer component is an unsaturated monomer having an electric charge, and 60 mol % or more of the second monomer component is an electrically neutral unsaturated monomer. In other words, by providing for this manner, it is made possible to introduce a large amount of electrically neutral unsaturated monomer into a first network structure which is formed by polymerizing and crosslinking a first monomer component and in which a group having an electric charge, for example, a carboxyl group, is present at a certain amount or more. In other words, the type and amount of monomer to be used and the sequence of uses are greatly important.

As an unsaturated monomer having an electric charge, an unsaturated monomers having an acidic group (for example, a carboxyl group, a phosphate group and a sulfonic group) and/or a basic group (for example, an amino group), such as 2-acrylamido-2-methylpropane sulfonic acid, acrylic acid, methacrylic acid or a salt thereof may preferably be mentioned.

As an electrically neutral unsaturated monomer, acrylamide, N-isopropyl acrylamide, vinylpyridine, styrene, methyl methacrylate, a fluorine-containing unsaturated monomer (for example, trifluoroethyl acrylate), hydroxyethyl acrylate or vinyl acetate may be mentioned for example.

The amount of the unsaturated monomer having an electric charge in the first monomer component is 10 mol % or more, and preferably 100 mol % in relation to the first monomer component. The amount of the unsaturated monomer having no electric charges in the second monomer component is 10 mol % or more, and preferably 100 mol % in relation to the second monomer component.

A second feature of this invention is that the molar ratio of the first monomer component to the second monomer component in the hydrogel is from 1:2 to 1:100, preferably 1:3 to 1:50, and more preferably 1:3 to 1:30. By providing for this manner, it is made possible to provide the gel with properties, such as mechanical strength, which have never been available heretofore. Introduction of an electrically neutral unsaturated monomer at such high ratios is made possible only by polymerizing and crosslinking a first monomer component to form a network structure (first network structure) in which a group having an electric charge (for example, a carboxylic group) is present at a certain amount or more, and then introducing the electrically neutral unsaturated monomer. When each network structure is composed of one monomer, the amount of monomer in the gel is determined by elemental analysis. When each network structure is composed of two or more monomers, it may be too complex to be determined by elemental analysis. In such cases, the amount is given by subtracting the amount of monomers which was not polymerized from the amount of monomers used for the production.

Further, a third feature of this invention is that when the second monomer component is polymerized and crosslinked, the degree of crosslinking is set to be lower than the degree of crosslinking of the first monomer component being polymerized and crosslinked. In other words, the degree of crosslinking of the second network structure (the network structure formed by polymerizing and crosslinking the second monomer component) is made lower than that of the first network structure, an extreme exemplification of which is the form of a hydrogel of a semi-interpenetrating network structure in which the degree of crosslinking of the second network structure is zero (that is, the second monomer component is polymerized, but not crosslinked). By providing for this manner, the gel can be provided with properties, such as mechanical strength, which have never been available heretofore. Conventionally, although gels in which the degree of crosslinking of a first network structure is lower than that of a second network structure have existed, such gels suffer from lack of mechanical strength. This invention is epoch-making in that the mechanical strength is greatly improved by merely reversing the relationship between the degrees of crosslinking of the first and second network structures.

Specifically, the amount of crosslinker used for the formation of the first network structure and that for the second network structure are adjusted as appropriate in relation to the starting monomers for the network structures. Provision is made so that preferably the first network structure has a degree of crosslinking of 0.1 to 50 mol % and the second network structure has a degree of crosslinking of 0.001 to 20 mol %, more preferably the first network structure has a degree of crosslinking of 1 to 20 mol % and the second network structure has a degree of crosslinking of 0.01 to 5 mol %, and most preferably the first network structure has a degree of crosslinking of 2 to 10 mol % and the second network structure has a degree of crosslinking of 0.05 to 1 mol %. In order to lower the water content of the gel (that is, to lower the degree of swelling) or to harden the gel (that is, to increase the elasticity) in particular, the degrees of crosslinking for the both structures may be increased.

Now that three features of this invention have been discussed, other optional construction requirements will then be described.

Firstly, the first monomer component is not particularly limited as long as it contains 10 mol % or more of an unsaturated monomer having an electric charge and, for example, an electrically neutral unsaturated monomer, which is indispensably used as a second monomer component, may be used. Also, the second monomer component is not particularly limited as long as it contains 60 mol % or more of an electrically neutral unsaturated monomer and, for example, an unsaturated monomer having an electric charge, which is indispensably used as a first monomer component, may be used. Examples include 2-acrylamido-2-methylpropane sulfonic acid (AMPS), acrylamide (AAm), acrylic acid (AA), methacrylic acid, N-isopropyl acrylamide, vinylpyridine, hydroxyethyl acrylate, vinyl acetate, dimethyl siloxane, styrene (St), methyl methacrylate (MMA) and trifluoroethyl acrylate (TFE). In addition, polysaccharides, such as gellan, hyaluronic acid, carageenan, chitin and alginic acid as well as proteins, such as gelatin and collagen may also be used. An organic polymer to be used may be identical or different among the first network structure, the second network structure (a hydrogel of an interpenetrating network structure) and the linear polymer (a hydrogel of a semi-interpenetrating network structure). When raw materials different from each other are used, hydrogels having higher dynamic properties will be obtained.

It is preferable to use as organic monomers as raw materials both water-insoluble monomers and water-soluble monomers. This is based on a novel finding that an excellent mechanical strength is afforded when a water-insoluble monomer is partly used. Such a water-insoluble monomer may be used for the first network structure only, for the second network structure (a hydrogel of an interpenetrating structure) or the linear polymer (a hydrogel of a semi-interpenetrating network structure) only or for the both. The ratio of the water-insoluble monomer to the water-soluble monomer is preferably 9.9:1.1 to 0.1:9.9. In particular, it is more preferable that the ratio of the water-soluble monomer to the water-insoluble monomer be 0:100 to 1:99 in the first network structure and 0:100 to 10:90 in the second network structure or the linear polymer. Moreover, it is even more preferable that the ratio of the water-soluble monomer to the water-insoluble monomer be 0:100 to 1:99 in the first network structure and 0:100 to 5:95 in the second network structure. In order to decrease the water content of the gel, the content of the hydrophobic monomer may be increased. Examples of water-insoluble monomers include fluorine-containing monomers, such as 2,2,2-trifluoroethyl methyl acrylate, 2,2,3,3,3-pentafluoropropyl methacrylate, 3-(perfluorobutyl)-2-hydroxypropyl methacrylate, 1H,1H,9H-hexadecafluorononyl methacrylate, 2,2,2-trifluoroethyl acrylate, 2,3,4,5,6-pentafluorostyrene and vinylidene fluoride.

Further, it is also preferable to use, as an organic monomer as a raw material, a monomer having a group capable of forming a complex with a metal ion and introduce a metal ion therefor into the gel to form a complex in the gel. In general, increasing the proportion of complex formation in the gel, that is, the metal introduction, can decrease the water content and increase the mechanical strength. In this case, the monomer having a group capable of forming a complex with a metal ion may be used for the first network structure only, for the second network structure (a hydrogel of an interpenetrating structure) or the linear polymer (a hydrogel of a semi-interpenetrating network structure) only or for the both. A preferable embodiment is one wherein a complex is formed with a metal ion in the first network structure. The metal content is preferably from 0.03 mol/l to 1 mol/l, and more preferably from 0.01 mol/l to 0.3 mol/l. The content of the monomer having a group capable of forming a complex is preferably from 10 to 100 mol %, and more preferably from 30 to 100 mol % in relation to the total monomer amount composing the first network structure. In addition, the ratio of the monomer having a group capable of forming a complex is preferably from 1:1 to 1:1000, and more preferably from 1:10 to 1:100. The metal ion is not particularly limited as long as it is capable of forming a complex, examples of which include zinc, iron, nickel, cobalt and chromium ions. A group capable of forming a complex with a metal ion refers to a group capable of forming a complex with a selected metal, examples of which include a carboxyl group, a sulfonic group and a phosphate group when a polyvalent metal, such as zinc, iron, nickel, cobalt or chromium is selected as a metal ion. As a monomer having a group capable of forming a complex with a metal ion, acrylic acid, methacrylic acid, itaconic acid, styrene sulfonic acid and vinyl phosphoric acid may be mentioned.

Physical properties of the hydrogel according to this invention will then be described.

First of all, this gel has a compression stress at rupture of preferably 1 to 100 MPa, more preferably 5 to 50 MPa, and most preferably 10 to 40 MPa. In addition, the gel has a tensile stress at rupture of preferably 0.1 to 100 MPa, more preferably 0.1 to 50 MPa, and most preferably 0.5 to 5 MPa.

Furthermore, the gel according to this invention has a water content of 10% or more, more preferably 50% or more, and even more preferably 85% or more. Thus, allowing the gel to have a large amount of water will improve flexibility and permeability for materials, which makes the gel useful for a DDS or application in which slow release properties may be needed. The upper limit of the water content is not particularly defined, but is usually 99.9% or less, preferably 99% or less, and more preferably 95% or less for the purpose of retaining mechanical strength, etc.

Also, the gel according to this invention has a degree of shrinkage of preferably 20 to 95%, more preferably 60 to 95%, and most preferably 70 to 95%. Since conventional gels show severe shrinkage upon immersion in saline water, they are deprived of applications as biomaterials. Having the physical properties as mentioned above is of great significance with respect to the provisions of possibilities for such applications. Such a low degree of shrinkage can provide advantages that the absorptive ability will not lessen when the gel is utilized in, for example, diapers. Usefulness is also found in utilizing the gel in seawater.

A process for producing the gel according to this invention will nextly be described. First, a solution containing a second monomer component (which contains 60% or more of an electrically neutral unsaturated monomer) and a polymerization initiator (as well as a crosslinker, in the case of a hydrogel of an interpenetrating network structure) is prepared. Subsequently, a gel having a first network structure (a single network gel formed by polymerizing and crosslinking a first monomer component which contains 10 mol % or more of an unsaturated monomer having an electric charge) is immersed in this solution and left for a sufficient period of time, during which the second monomer component and the polymerization initiator (as well as a crosslinker, in the case of a hydrogel of an interpenetrating network structure) will diffuse into the gel. The gel is then removed from the solution, and the second monomer component in the gel is polymerized (and crosslinked, in the case of a hydrogel of an interpenetrating network structure) to thereby form a second network structure (in the case of a hydrogel of an interpenetrating network structure) or a linear polymer (in the case of a semi-interpenetrating network structure) so that a gel having a double network structure may be produced. In addition, it is also possible to produce, in a similar manner to the above procedure, a gel of a triple or more interpenetrating network structure, by using a gel having a multi-network structure instead of a single-network type gel as described above.

Polymerization initiators to be used for forming the first network structure, the second network structure (in the case of a gel of an interpenetrating network structure) and the linear polymer (in the case of a semi-interpenetrating network structure) are not particularly limited and a variety of them may be used depending on the organic monomers to be polymerized. For example, a water-soluble thermal catalyst such as potassium persulfate or a redox initiator such as potassium persulfate-sodium thiosulfate may be used in the case of thermally polymerizing AMPS, AAm or AA as an organic monomer, and 2-oxoglutaric acid may be used as a photosensitizer in the case of photopolymerization. In addition, thermal catalysts that are soluble in organic solvents, such as azobisisobutyronitrile (AIBN) and benzoyl peroxide (BPO) may be used in the case of thermally polymerizing St as an organic monomer, and benzophenone as a photosensitizer may be used in the case of photopolymerization.

Similarly, crosslinkers to be used for forming the first network structure and the second network structure (in the case of a gel of an interpenetrating network structure) are not particularly limited and a variety of them may be selected depending on the organic monomers to be crosslinked. For example, N,N'-methylenbisacrylamide and ethylene glycol dimethacrylate may be used in the case of using AMPS, Am or AA as an organic monomer and in the case of using St as an organic monomer, respectively.

In addition, the solvent for the solution for immersing the gel having the first network structure is preferably the same as the solvent in the gel having the first network structure, in view of that any adverse effect on the gel to be immersed in the solution may be prevented and the double-network structure (a hydrogel of an interpenetrating network structure) and the linear polymer (a hydrogel of an semi-interpenetrating structure) may be entwined well with the network of the first network structure. The solvent to be eventually contained in the gel (water) may be water as a solvent from the production stage or may be water which replaces a solvent after production.

With respect to the embodiment wherein a metal ion is introduced in the gel, the obtained hydrogel of a (semi)interpenetrating network structure is dried in vacuo and then immersed in the metal salt solution. According to this manipulation, a complex may efficiently be formed with the metal ion by reducing the distance between the networks.

Conditions, etc. for polymerization and crosslinking will then be described. First, polymerization reaction of the first monomer component diffused throughout the gel having the first network structure may be made either by heating or by irradiation with light such as ultraviolet radiation. The polymerization reaction is conducted under such conditions that the first network structure of the gel may not be destroyed. Also for the polymerization reaction, a crosslinker and a reaction initiator at predetermined concentrations, together with the second monomer component, are mixed into the solvent to diffuse throughout the gel having the first network structure. Specifically, the gel having the first network structure is immersed in the second monomer solution containing the crosslinker to diffuse at a low temperature for 24 hours. In order to avoid crosslinking during diffusion, a temperature at or below the room temperature, or around 4° C., is preferred.

Finally, applications of the gel according to this invention will be described. The gel exhibits high compression and tensile stresses at rupture and a chemical resistance, and possesses flexibility, permeability for materials and impact resistance as a gel so that the gel has a wide range of applications as water-absorbing materials, water-retaining materials, industrial materials and biosubstitution materials. Specifically, diapers, sanitary products, sustained-release agents, construction materials, building materials, communication materials (for example, bearings, cables, couplings therefor), soil conditioners, contact lenses, intraocular lenses, hollow fibers, artificial cartilages, artificial joints, artificial organs (for example, artificial blood vessels, artificial skins), materials for fuel cells, battery diaphragms, impact-resistant materials and cushions may be mentioned. In particular, usefulness of the gel according to this invention is great with respect to absorbing materials (for example, diapers, construction materials) for which a strength of 1 MPa or more is required, contact lenses and intraocular lenses for which a strength of 5 MPa or more is required and artificial kidneys (hollow fibers) for which a strength of 10 MPa or more is required, because gels have never existed having such strengths at a solvent content of 10% or more.

EXAMPLES

This invention is specifically demonstrated using Examples below.

Example 1

Preparation of Single-Network Type Gel

From a silicone plate having an area of 100 mm×100 mm and a thickness of 2 mm, a frame having outer sides of 80 mm×80 mm and a width of 5 mm was cut out and a groove of 3 mm was bored on a location on the frame. The silicone frame was interposed between two glass plates each having an area of 100 mm×100 mm and a thickness of 3 mm to assemble a polymerization reactor.

25 ml of 2 mol/l aqueous solution of 2-acrylamido-2-methylpropane sulfonic acid (AMPS) as a monomer, 1 ml of 2 mol/l aqueous solution of N,N'-methylenebisacrylamide (MBAA) as a crosslinker and 1 ml of 0.1 mol/l aqueous solution of 2-oxoglutaric acid as an initiator were combined and conditioned with water to obtain 50 ml of an aqueous solution. The solution was then deoxygenated using a nitrogen gas. Subsequently, the deoxygenated solution was poured into an opening of the silicone plate placed on one of the glass plates of the polymerization reactor and the other glass plate was superposed on the silicone plate to seal around the opening. Afterward, polymerization was carried out using a UV lamp having a wavelength of 365 nm (22 W, 0.34 A) to irradiate ultraviolet radiation at a normal temperature for six hours to prepare an AMPS gel (a first network structure) having a degree of crosslinking of 4 mol %. The degree of crosslinking was calculated as follows:

{(aqueous $MBAA$ solution concentration × amount)/

(monomer concentration × amount)} × 100 =

{(2 mol/l × 1 ml)/(2 mol/l × 25 ml)} × 100 = 4 mol %.

Preparation of Double-Network Type Gel 40 ml of 5 mol/l aqueous solution of acrylamide as a monomer, 1 ml of 0.2 mol/l aqueous solution of N,N'-methylenebisacrylamide (MBAA) as a crosslinker and 1 ml of 0.1 mol/l aqueous solution of 2-oxoglutaric acid as an initiator were combined and conditioned with water to obtain 200 ml of an aqueous solution (immersion solution). The immersion solution was then deoxygenated using a nitrogen gas.

Subsequently, the immersion solution and 4 g of the single-network type gel were placed in a sealed container having a sufficiently larger volume than the gel. The container was stored in a refrigerator at 4° C. for 24 hours to allow the monomer, the crosslinker and the initiator in the immersion solution to diffuse and penetrate into the gel. During the step, the container was gently shaken occasionally for the purpose of evening out the concentration of the immersion solution.

Next, the gel was removed from the immersion solution, cut to an appropriate size and then held between two glass plates of 100 mm in width, 100 mm in length and 3 mm in thickness, avoiding inclusion of bubbles. After sealing four peripheral sides of the two glass plates, a UV lamp having a wavelength of 365 nm (22 W, 0.34 A) was used to irradiate ultraviolet radiation at a normal temperature for six hours, during which the AAm monomer diffused throughout the gel was polymerized to give a double-network type gel. The second network structure of the double-network type gel had a degree of crosslinking of 0.1 mol %. The degree of crosslinking was calculated as follows:

{(2 mol/l×1 ml)/(5 mol/l×40 ml)}×100=0.1 mol %.

The double-network type gel of AMPS-AAm obtained in Example 1 was equilibrated and swollen in pure water. Elemental analysis was conducted on the gel. The results are shown in Table 1 below.

TABLE 1

|  |  | C (%) | H (%) | N (%) |
|---|---|---|---|---|
| double-network type gel | theoretical | 50.30 | 6.29 | 9.78 |
|  | found | 48.98 | 6.60 | 9.49 |

As seen clearly from Table 1 above, it was confirmed that the AAm monomer which was used for the second polymerization was crosslinked in the double-network type gel without exiting the gel through equilibrium and swelling, because nitrogen shows a value of 9.49% in relation to the total amount of both the AMPS and AAm monomers.

Example 2

Preparation of Single-Network Type Gel 40 ml of 2 mol/l aqueous solution of acrylic acid (AA) as a monomer, 4 ml of 0.2 mol/l aqueous solution of N,N'-methylenebisacrylamide (MBAA) as a crosslinker and 1 ml of 0.1 mol/l aqueous solution of 2-oxoglutaric acid as an initiator were combined and conditioned with water to obtain 50 ml of an aqueous solution. The solution was then deoxygenated using a nitrogen gas. Subsequently, the deoxygenated solution was poured into an opening of a silicone plate placed on one of glass plates of a polymerization reactor similar to one in Example 1 and the other glass plate was superposed on the silicone plate to seal around the opening. Afterward, polymerization was carried out using a UV lamp having a wavelength of 365 nm (22 W, 0.34 A) to irradiate ultraviolet radiation at a normal temperature for six hours to prepare an AA gel having a degree of crosslinking of 1 mol %.

Preparation of Double-Network Type Gel 20 ml of 5 mol/l aqueous solution of acrylamide (AAm) as a monomer, 1 ml of 0.1 mol/l aqueous solution of N,N'-methylenebisacrylamide (MBAA) as a crosslinker and 1 ml of 0.1 mol/l aqueous solution of 2-oxoglutaric acid as an initiator were combined and conditioned with water to obtain 200 ml of an aqueous solution (immersion solution). The immersion solution was then deoxygenated using a nitrogen gas.

Subsequently, the immersion solution and 4 g of the single-network type gel were placed in a sealed container having a sufficiently larger volume than the gel. The container was stored in a refrigerator at 4° C. for 24 hours to allow the monomer, the crosslinker and the initiator in the immersion solution to diffuse and penetrate into the gel. During the step, the container was gently shaken occasionally for the purpose of evening out the concentration of the immersion solution.

Next, the gel was removed from the immersion solution, cut to an appropriate size and then held between two glass plates of 100 mm in width, 100 mm in length and 3 mm in thickness, avoiding inclusion of bubbles. After sealing four peripheral sides of the two glass plates, a UV lamp having a wavelength of 365 nm (22 W, 0.34 A) was used to irradiate ultraviolet radiation at a normal temperature for six hours, during which the AAm monomer diffused throughout the gel was polymerized to give a double-network type gel. The second network structure of the double-network type gel had a degree of crosslinking of 0.1 mol %.

Test Example 1

Degree of swelling, compression stress at rupture and compression strain at rupture were determined for the double-network type gels obtained in Examples 1 and 2 and, for comparison, the single-network type gels prepared in Examples 1 and 2. The results are shown in Table 2 (single-network type gels) and 3 (double-network type gels).

TABLE 2

| monomer for polymerization, degree of crosslinking in parentheses | AMPS (15 mol %) | AA (2 mol %) |
|---|---|---|
| degree of swelling | 12 | 90 |
| compression stress at rupture (MPa) | 0.9 | 0.1 |
| compression strain at rupture (%) | 30 | 63 |

TABLE 3

| Ex. | degree of crosslink of first network structure (mol %) | degree of crosslink of second network structure (mol %) | comp. stress at rupture (MPa) | comp. strain at rupture (%) | water content | degree of shrinkage | monomer ratio 1st:2nd |
|---|---|---|---|---|---|---|---|
| 1 | 4 | 0.1 | 9.7 | 82 | 92 | 78 | 1:10 |
| 2 | 1 | 0.1 | 3 | 95 | 91 | 80 | 1:15 |

As clearly seen from Tables 2 and 3 above, it is found that the double-network type gel of AMPS-AAm of Example 1 has a higher compression stress at rupture in comparison with the AMPS single-network type gel. In addition, it is seen that the AA-AAm double-network type gel of Example 2 has a remarkably higher compression stress at rupture in comparison with the AAm single-network type gel.

Example 3

Figure 3:
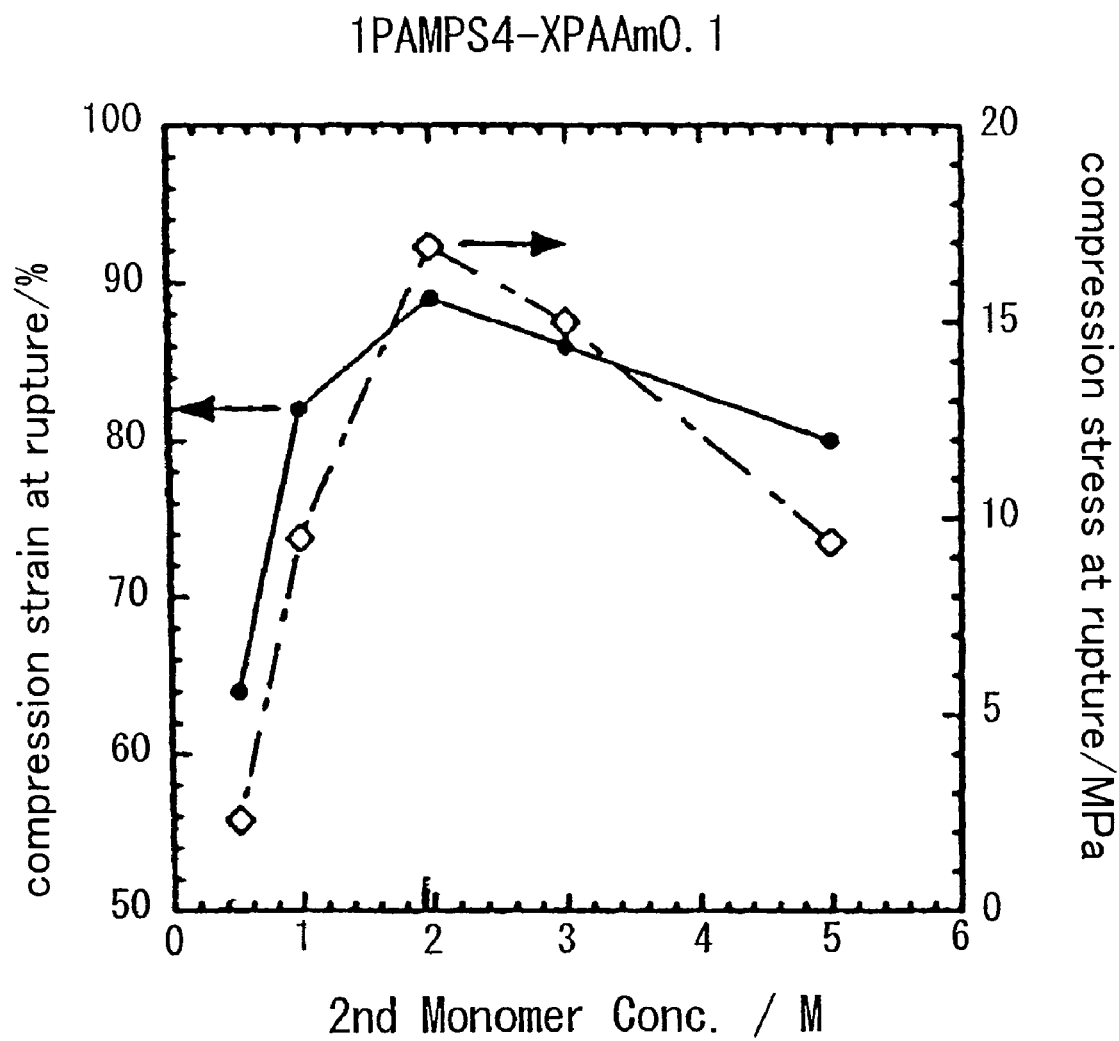
FIG. 3 shows the dependency on concentration of the monomer composing the second network structure in relation to compression stress and strain at rupture in a 1PAMPS4-XPAAm0.1 DN gel, wherein the second monomer concentration along the abscissa refers to the concentration of the second monomer used for polymerization, to which X in "1PAMPS-XPAAm0.1" corresponds.
Figure 4:
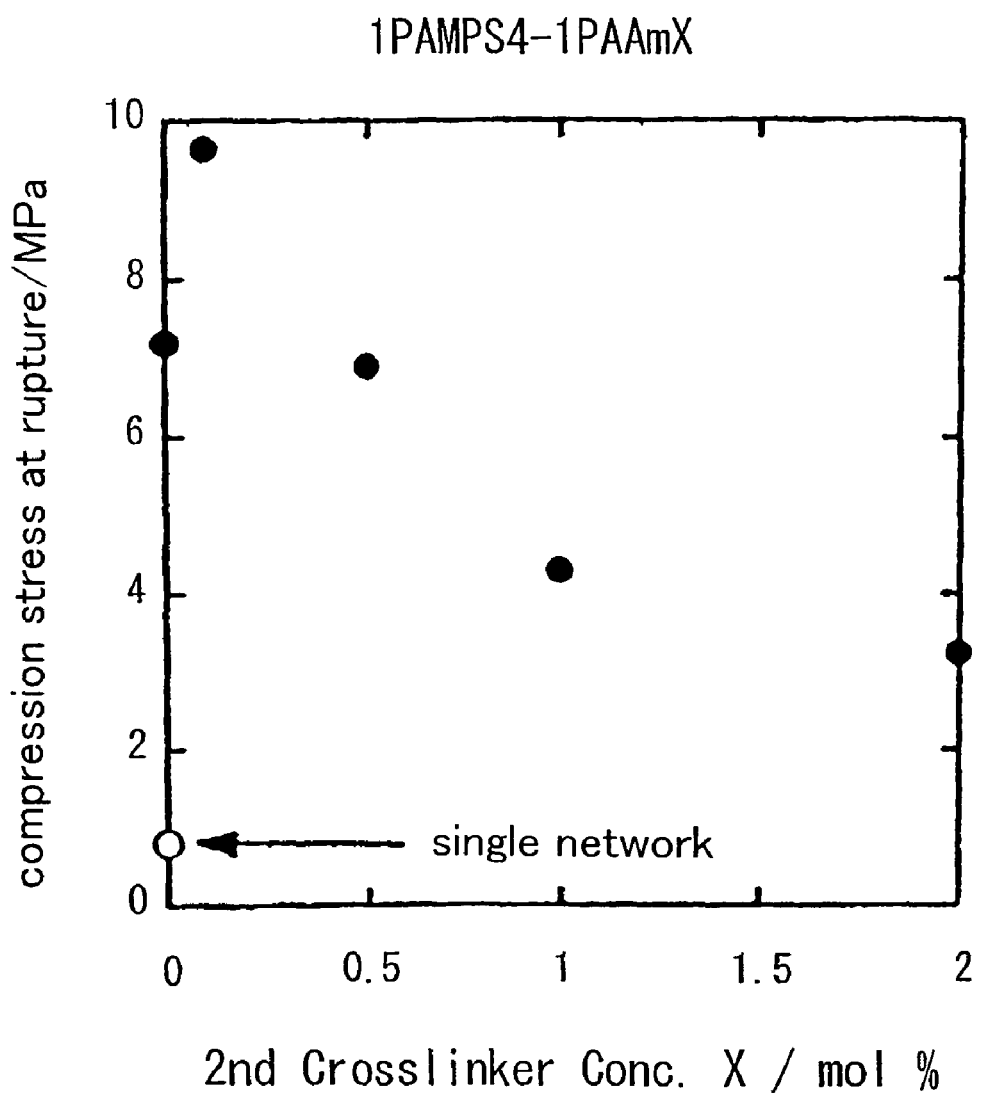
FIG. 4 shows the dependency on degree of crosslinking of the second network structure in relation to compression stress at rupture in a 1PAMPS4-1PAAmX DN gel.

In a similar manner as Example 1, but altering the ratio between the monomers composing the first and second network structures and also altering the degrees of crosslinking of the first and second network structures, mechanical strength was determined. Hereinbelow, an abbreviated designation is used for each double-network type gel, consisting of first monomer concentration (M), monomer name and degree of crosslinking (mol %)-second monomer concentration (M), monomer name and degree of crosslinking (mol %) in the mentioned order. By way of illustration, a double-network type gel in which a first network structure is PAMS having a monomer concentration of 1 M and a degree of crosslinking of 4 mol %, and a second network structure is PAAm having a monomer concentration of 1 M and a degree of crosslinking of 0.1 mol % is designated as 1PAMPS4-1PAAm0.1. It should be noted that the monomer concentrations here are those at the time of production and differ from the monomer amounts in the final gel. In other words, when the concentrations of the first and second monomers are both 1 M for example, their molar ratio in the final gel obtained will not be 1:1. It is understood that the first network structure has an electric charge, and therefore, swells largely in the neutral solution of the second monomer in water. (In this Example, the monomer amount in the final gel is AMPS:AAm=1:10.) The results are shown in Table 4 and FIGS. 3 and 4. From Table 4 and FIG. 3, it is seen that, for the double-network type gel based on PAMPS-PAAm, when the composition ratio between the monomers in the first and second network structures is altered, the breaking strength is the highest at the monomer in the first network structure (PAMPS):the monomer in the second network structure (PAAm)=1:20. Also, from FIG. 4, it is seen that the strength varies depending on the degree of crosslinking of the second network structure (PAAm) and reaches the highest when the degree is 0.1 mol %.

TABLE 4

| sample name | PAMPS:PAAm | degree of swelling | initial modulus (MPa) | breaking strength (MPa) | breaking strain (%) |
|---|---|---|---|---|---|
| 1PAMPS4-0.5PAAm0.1 | 1:6 | 13 | 0.41 | 2.3 | 64 |
| 1PAMPS4-1PAAm0.1 | 1:10 | 12 | 0.37 | 9.5 | 82 |
| 1PAMPS4-2PAAm0.1 | 1:20 | 6.9 | 0.60 | 17 | 89 |
| 1PAMPS4-3PAAm0.1 | 1:30 | 5.2 | 0.75 | 15 | 86 |
| 1PAMPS4-5PAAm0.1 | 1:53 | 4.9 | 0.90 | 9.4 | 80 |

Example 4

First Network

AMPS and TFEA were mixed at a ratio of 1:5 into DMSO to a concentration of 3.0 ml/l, 1 mol % of a crosslinker MBAA and 0.2 mol % of a polymerization initiator α-ketoglutaric acid were added and synthesis was carried out by UV polymerization.

Second Network 10 ml of the above gel were immersed in 200 ml of a solution of TFEA in DMSO (concentration 3.0 ml/l, MBAA 0.1 mol % and α-ketoglutaric acid 0.2 mol %) and left for approximately two days and synthesis was carried out by UV polymerization. Physical properties of the gel obtained in this manner are shown in Table 9.

TABLE 5

| Ex. | degree of crosslink of first network structure (mol %) | degree of crosslink of second network structure (mol %) | tensile stress at rupture (MPa) | tensile strain at rupture (%) | water content (%) | degree of shrinkage (%) | monomer ratio 1st:2nd |
|---|---|---|---|---|---|---|---|
| 4 | 1.0 | 0.1 | 2.2 | 410 | 29 | 100 | 1:6 |

Example 5

Various metal ions were introduced into the double-network type gel of 1PAMPS4-1PAAm0.1 obtained in Example 3 and mechanical strength was determined. For the purpose of introducing the metal ions, the double-network type gel equilibrated and swollen in pure water was cut out to an appropriate size and once dried in vacuo. Aqueous solutions of various metal salts were then prepared in amounts 20-fold in relation to the volume of the gel as equilibrated and swollen, in which the gel was immersed for approximately one week. The aqueous solutions were prepared in three concentrations of 0.01 M, 0.1 M and 1 M for $ZnSO_4$ and three concentrations of 0.01 M, 0.1 M and 0.3 M for $FeCl_3$. The results are shown in Table 6.

TABLE 6

| | degree of swelling | initial modulus (MPa) | stress at rupture (MPa) | strain at rupture (%) | water content (%) | degree of shrinkage (%) |
|---|---|---|---|---|---|---|
| reference (swollen in pure water) | 12 | 0.35 | 0.7 | 100 | 92 | 78 |
| $Zn^{2+}$ (0.01 M) | 9 | 0.25 | 1.0 | 100 | 89 | 75 |
| $Zn^{2+}$ (0.1 M) | 7 | 0.31 | 14.8 | 89 | 86 | 58 |
| $Zn^{2+}$ (1 M) | 3 | 0.30 | 17.6 | 88 | 67 | 25 |
| $Fe^{3+}$ (0.01 M) | 4 | 0.21 | 41.2 | 95 | 75 | 33 |
| $Fe^{3+}$ (0.1 M) | 6 | 0.14 | 15.8 | 88 | 83 | 50 |
| $Fe^{3+}$ (0.3 M) | 6 | 0.13 | 14.2 | 88 | 83 | 50 |

Test Example 2

Stress Dispersibility Test

According to a similar procedure as the above, various double-network type hydrogels of PAMPS-PAAm were prepared. These hydrogels were cut to 60×30×10 mm.

Figure 5:
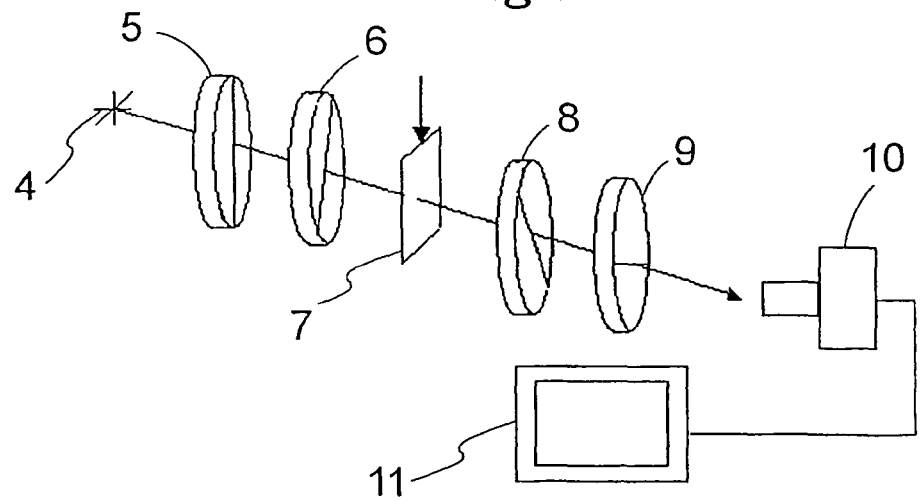
FIG. 5 shows an experimental system for taking pictures of photoelastic images as a gel is deformed under stress, wherein 4 denotes a light source, 5 denotes a polarizer, 6 and 8 denote ¼ plates, 7 denotes a specimen, 9 denotes an analyzer, 10 denotes a CCD camera and 11 denotes a computer.

Test system used for this occasion is shown in FIG. 5. As a light source 4, a He—Ne laser (Model 127, Spectra-Physics Laser, Inc.) was used. The axis of a polarizer 5 was vertically oriented and the axis of an analyzer 9 was horizontally oriented. The fast axes of two ¼ plates 6 and 8 were set at n/4 and −n/4 radians respectively in relation to the axes of the polarizer 5 and the analyzer 9. Photoelastic images were recorded with a cooled CCD camera (C4742-95, Hamamatsu Co., Japan) linked with a personal computer 11 (the entire image area includes 1280×1024 pixels).

Figure 6:
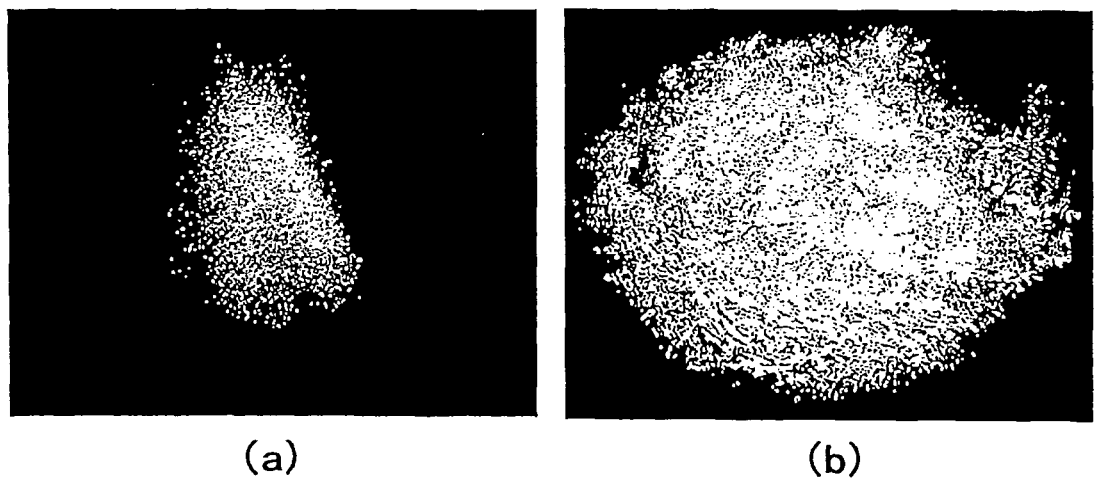
FIG. 6 shows photoelastic images representing stress diffusions for various gels as the gels are deformed under stress, wherein (a) is from a 1PAMPS4-1PAAm0.1 DN gel and (b) is from a 1PAMPS4-1PAAm2 DN gel.

Image views showing the degree of stress dispersion photographed by this CCD camera are shown in FIG. 6. Discolored areas (which appear white in the views) imply the concentration of stress. As seen therefrom, the image (a) of the PAMPS-PAAm hydrogel (the degree of crosslinking of PAAm is 0.1 mol %) has less discolored areas in comparison with the image (b) of the PAMPS-PAAm hydrogel (the degree of crosslinking of PAAm is 2 mol %). Thus, it is seen that the hydrogel according to this invention, of which the dynamic strength is optimized, is excellent in stress dispersibility.

Figure 7:
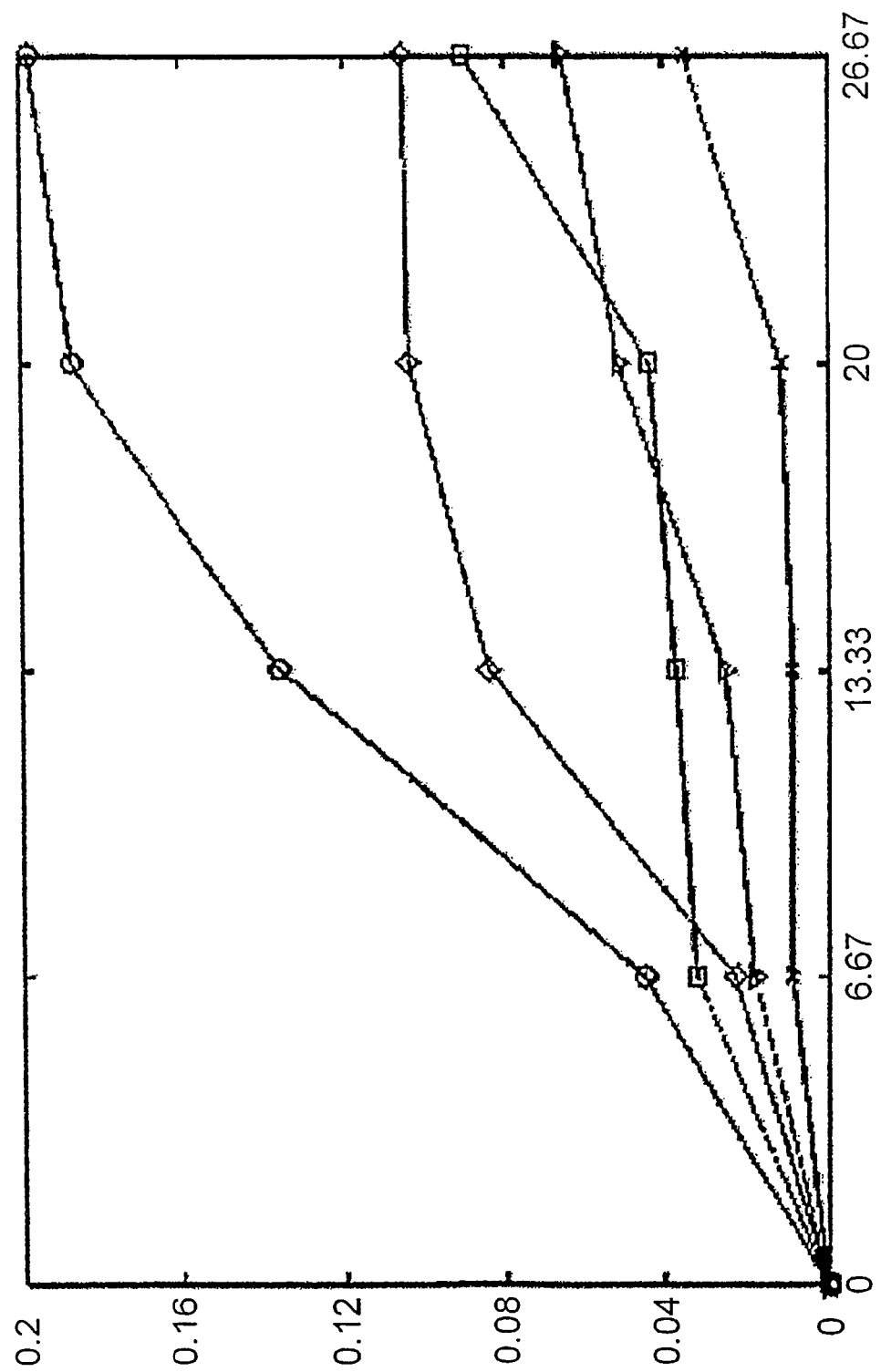
FIG. 7 shows the relationship between Normalized Power (ordinate) and strain (%) as 1PAMS4-1PAAmX DN gels (X=0, 0.1, 0.5, 1.0 and 2.0 mol %) are deformed under stress, wherein "□" is for X=0 mol %, "x" is for X=0.1 mol %, "∇" is for X=0.5 mol %, "◇" is for X=1.0 mol % and "o" is for X=2.0 mol %.
Figure 8:
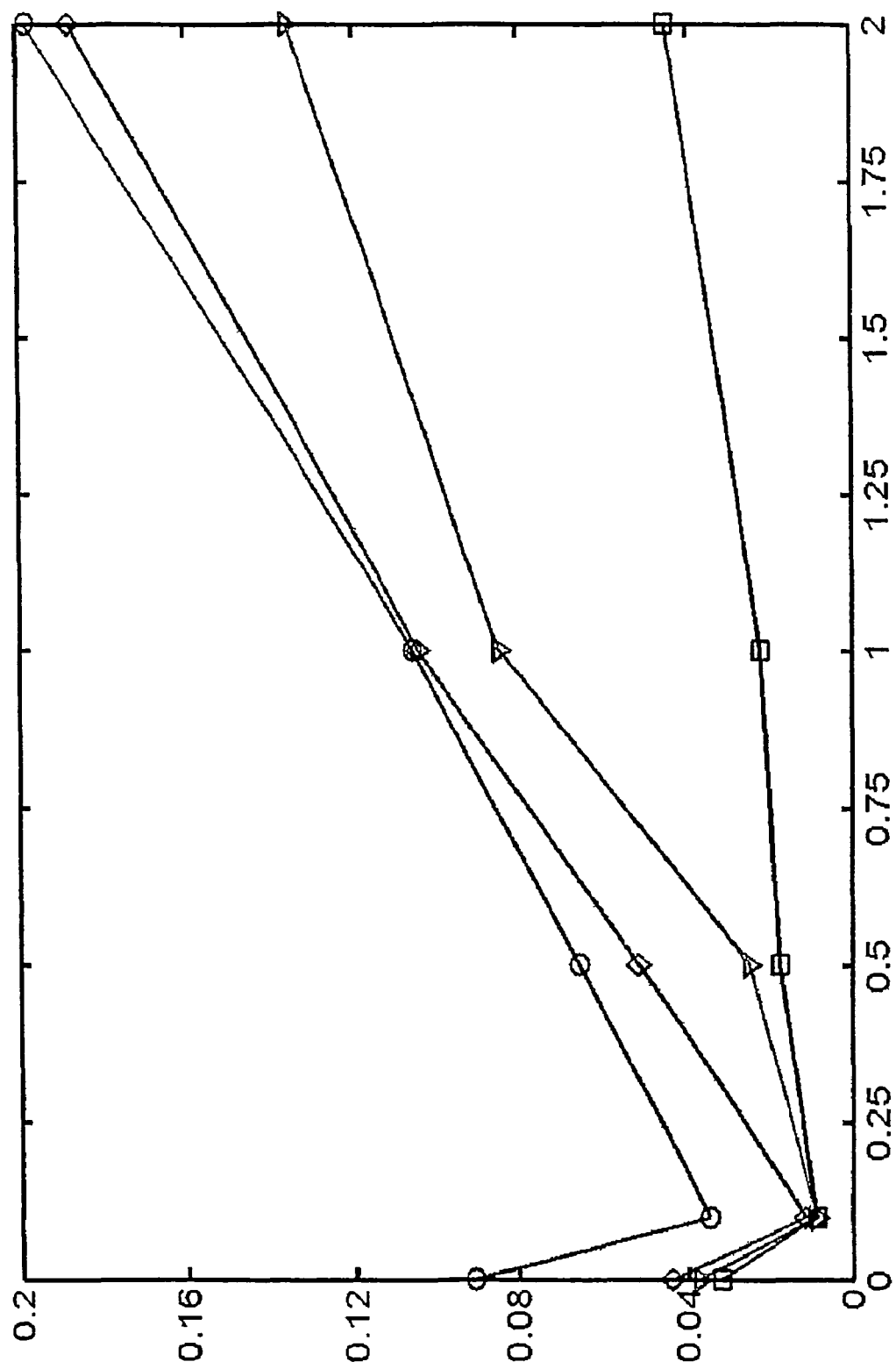
FIG. 8 shows the relationship between Normalized Power (ordinate) and degree of crosslinking (mol %) as 1PAMS4-1PAAmX DN gels (X=0, 0.1, 0.5, 1 and 2 mol %) are deformed under stress, wherein "□" is for strain of 6.670%, "∇" is for strain of 13.33%, "◇" is for strain of 20.22% and "o" is for strain of 26.67%.

In addition, normalized power and strain were tested but altering the degree of crosslinking of PAAm (0.0 mol %, 0.1 mol %, 0.5 mol %, 1.0 mol % and 2.0 mol %). The results are shown in FIG. 7. From FIG. 7, it is seen that there is a trend that the lower the degree of crosslinking of the second network structure is, the better the stress is dispersed at an identical strain and the less the normalized power is. In addition, FIG. 8 illustrates the relationship between the normalized power and the degree of crosslinking and it is seen from this drawing that the normalized power is the lowest when the degree of crosslinking is around 0.1 mol % with respect to any strain.

Figure 9:
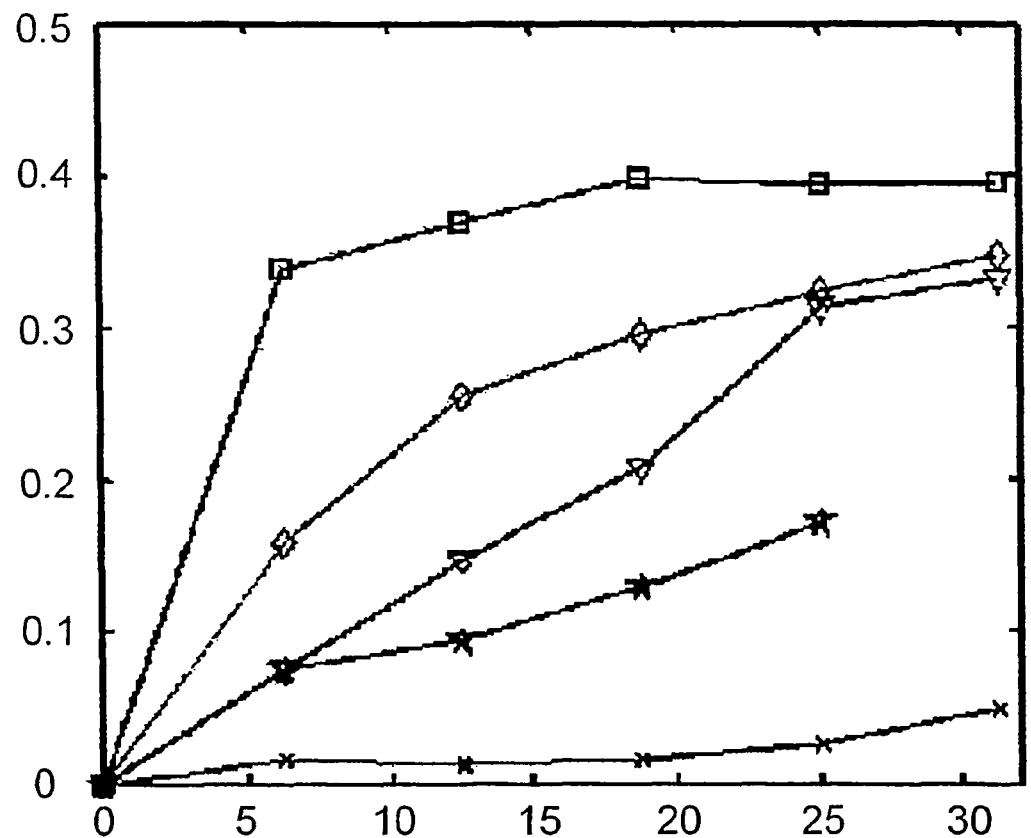
FIG. 9 shows the relationship between Intensity (ordinate) and strain (%) as various 1PAMS4-XPAAm0.1 DN gels having different AAm concentrations are deformed under stress, wherein "*" is for X=0.5 M, "x" is for X=1 M, "∇" is for X=2 M, "◇" is for X=3 M and "□" is for X=5 M.

Finally, intensity and strain were tested, altering the concentration of AAm (0.5 M, 1 M, 2 M, 3 M and 5 M) while fixing the degree of crosslinking (0.1 mol %). The results are shown in FIG. 9. It is seen from this drawing that the intensity tends to be higher at an identical strain when the concentration of AAm is higher and that the intensity is the lowest when the concentration of AAm is 1 M. In other words, the DN gel, of which the dynamic strength is optimized, has the highest capability of dispersing stress.

The invention claimed is:

1. A hydrogel of an interpenetrating network structure wherein a first network structure is uniformly entwined with a second network structure throughout the gel, obtained by polymerizing and crosslinking a first monomer component to form the first network structure; introducing a second monomer component into the first network structure; and polymerizing and crosslinking the second monomer component to form the second network structure entwined with the first network structure, characterized in that 10 mol % or more of the first monomer component is an unsaturated monomer having an electric charge selected from the group consisting of 2-acrylamido-2-methylpropane sulfonic acid, acrylic acid, methacrylic acid, and a salt thereof, 60 mol % or more of the second monomer component is an electrically neutral unsaturated monomer selected from the group consisting of acrylamide, N-isopropyl acrylamide, vinylpyridine, styrene, methyl methacrylate, a fluorine-containing unsaturated monomer, hydroxyethyl acrylate and vinyl acetate, the molar ratio of the first monomer component to the second monomer component is from 1:2 to 1:100, and after the second monomer component is polymerized and crosslinked, the degree of crosslinking is set to be lower than the degree of crosslinking of the first monomer component being polymerized and crosslinked.

2. The hydrogel according to claim 1, wherein the hydrogel further contains a metal ion, and at least part of the first monomer component and the second monomer component has a group capable of forming a complex with the metal ion.

3. The hydrogel according to claim 1, wherein the first network structure based on the first monomer component has a degree of crosslinking of 0.1 to 50 mol % and the second network structure based on the second monomer component has a degree of crosslinking of 0.001 to 20 mol %.

4. The hydrogel according to claim 1, which has a water content of 10% or more.

5. The hydrogel according to claim 1, which has a compression stress at rupture of 1 to 100 MPa.

6. The hydrogel according to claim 1, which has a tensile stress at rupture of 1 to 100 MPa.

7. An article comprising the hydrogel as defined in claim 1.

8. A process for producing a hydrogel of an interpenetrating network structure wherein a first network structure is uniformly entwined with a second network structure throughout the gel, comprising the steps of:

polymerizing and crosslinking a first monomer component, of which 10 mol % or more is an unsaturated monomer having an electric charge selected from the group consisting of 2-acrylamido-2-methylpropane sulfonic acid, acrylic acid, methacrylic acid, and a salt thereof, to form a first network structure; and introducing a second monomer component, of which 60 mol % or more is an electrically neutral unsaturated monomer selected from the group consisting of acrylamide, N-isopropyl acrylamide, vinylpyridine, styrene, methyl methacrylate, a fluorine-containing unsaturated monomer, hydroxyethyl acrylate and vinyl acetate, into the first network structure and then polymerizing and crosslinking the second monomer component thereby to form a second network structure in the first network structure, wherein, crosslinker is used for each polymerization whereby, after the second monomer component is polymerized and crosslinked, the degree of crosslinking is set to be lower than the degree of crosslinking of the first monomer component being polymerized and crosslinked, the degree of crosslinking of the first network being 0.1 to 50 mol % and the degree of crosslinked of the second network structure being 0.001 to 20 mol %; and wherein the molar ratio of the first monomer component to the second monomer component is from 1:2 to 1:100.

9. The process according to claim 8, wherein the hydrogel further contains a metal ion, and at least part of the first monomer component and the second monomer component has a group capable of forming a complex with the metal ion.

10. The process according to claim 8, wherein the hydrogel has a water content of 10% or more.

11. The process according to claim 8, wherein the hydrogel has a compression stress at rupture of 1 to 100 MPa.

12. The process according to claim 8, wherein the hydrogel has a tensile stress at rupture of 0.1 to 100 MPa.

13. The hydrogel according to claim 1, wherein 100 mol % of the first monomer component is an unsaturated monomer having an electric charge and 100 mol % of the second monomer component is an electrically neutral unsaturated monomer.

14. The process according to claim 8, wherein 100 mol % of the first monomer component is an unsaturated monomer having an electric charge and 100 mol % the second monomer component is an electrically neutral unsaturated monomer.

* * * * *